United States Patent [19]

Junino et al.

[11] Patent Number: 4,666,453
[45] Date of Patent: May 19, 1987

[54] NITRO-META-PHENYLENEDIAMINES HALOGENATED IN THE 6TH POSITION AND THEIR USE IN DYEING KERATINIC SUBSTANCES

[75] Inventors: Alex Junino, Livry-Gargan; Gerard Lang, Saint Gratien; Ginette Jeanminet, Aulnay-sous-Bois, all of France

[73] Assignee: L'Oreal, Paris, France

[21] Appl. No.: 872,401

[22] Filed: Jun. 10, 1986

[30] Foreign Application Priority Data

Jun. 10, 1985 [LU] Luxembourg ............... 85939

[51] Int. Cl.⁴ ............... A61K 7/13; C07C 87/60; C07C 87/58; C07C 85/04
[52] U.S. Cl. ............... 8/415; 8/407; 8/408; 8/411; 8/414; 564/367; 564/368; 564/369; 564/371; 564/441
[58] Field of Search ............... 8/407, 408, 409, 411, 8/414, 415; 564/441; 564/367, 368, 369, 371

[56] References Cited

U.S. PATENT DOCUMENTS

| | | | |
|---|---|---|---|
| 2,087,689 | 7/1937 | Knecht et al. | 564/441 |
| 2,621,175 | 12/1952 | Holly et al. | 564/441 |
| 3,658,885 | 4/1972 | Lange et al. | 564/441 |
| 3,743,678 | 7/1973 | Halasz et al. | 564/441 |
| 3,904,690 | 9/1975 | Kalopissis et al. | 8/415 |
| 4,018,556 | 4/1977 | Kalopissis et al. | 8/415 |
| 4,172,098 | 10/1979 | Scheuermann et al. | 564/441 |
| 4,601,726 | 7/1986 | Grollier et al. | 8/414 |

FOREIGN PATENT DOCUMENTS

| | | |
|---|---|---|
| 226679 | 4/1963 | Austria . |
| 0132568 | 2/1985 | European Pat. Off. . |
| 1619615 | 10/1966 | Fed. Rep. of Germany . |
| 798141 | 5/1936 | France . |
| 1174816 | 12/1969 | United Kingdom . |
| 1286738 | 8/1972 | United Kingdom . |

OTHER PUBLICATIONS

Lambie et al., *Chemical Abstracts*, 32452y, vol. 67, 1967, p. 3057, 3058.
Adams, R. et al., "Quinone Imides, XXV, Addition of Mercaptans to P-Quinonedibenzenesulfonimide", *J. Am. Chem. Soc.*, vol. 7, Feb. 5, 1953, pp. 663-666.

*Primary Examiner*—Paul Lieberman
*Assistant Examiner*—L. Skaling
*Attorney, Agent, or Firm*—Fleit, Jacobson, Cohn & Price

[57] ABSTRACT

The invention relates to compounds of formula

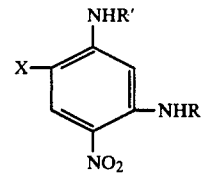

in which X denotes a halogen atom, and R and R' denote a hydrogen atom, an alkyl, polyhydroxyalkyl, hydroxyalkoxyalkyl or alkoxyalkyl radical or an aminoalkyl radical optionally substituted on the nitrogen atom provided that at least one of the groups R and R' is a polyhydroxyalkyl, alkoxyalkyl or hydroxyalkoxyalkyl radical, and to dye compositions for keratinic fibres in which they are employed, to the preparation process and to intermediates.

24 Claims, No Drawings

NITRO-META-PHENYLENEDIAMINES HALOGENATED IN THE 6TH POSITION AND THEIR USE IN DYEING KERATINIC SUBSTANCES

The present invention relates to new nitro-meta-phenylenediamines halogenated in the 6 position, to a process for their preparation and to the dye compositions for keratinic fibres, especially human hair, in which they are present.

Direct dyes from the group of nitro derivatives of the benzene series have been used for many years in what is known as a semi-permanent process for dyeing hair. Such direct dyes are also used in oxidation dyeing or what is known as "permanent" dyeing with a view to adding highlights to basic colours produced with the precursors of oxidation dyes.

The inventors have found new yellow dyes which may be used in direct dyeing or in oxidation dyeing to add complementary highlights to the base colour. These new compounds endow hair with colours which are stable to washing, to light and to bad weather and are especially remarkable in their good washing resistance.

The subject of the invention is therefore new nitro dyes of the benzene series.

Another subject of the invention consists of the dye compositions in which they are present and the dyeing processes in which they are used.

Other subjects will become apparent from reading the description and the examples which follow.

The new compounds according to the invention correspond to the formula:

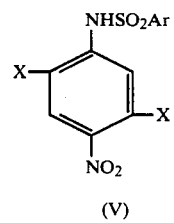
(I)

in which X denotes a halogen atom chosen from chlorine, bromine and fluorine; R and R' denote a hydrogen atom, a $(C_1-C_6)$alkyl, polyhydroxy$(C_2-C_6)$alkyl, hydroxy$(C_2-C_4)$alkoxy$(C_1-C_4)$alkyl, $(C_1-C_3)$alkoxy$(C_1-C_6)$alkyl radical or an amino$(C_1-C_6)$alkyl radical optionally substituted on the nitrogen atom, provided that at least one of the groups R or R' is a polyhydroxyalkyl, alkoxyalkyl or hydroxyalkoxyalkyl radical. The substituents on the nitrogen atom are preferably chosen from $(C_1-C_4)$alkyl and hydroxy$(C_1-C_4)$alkyl groups.

Among the preferred groups R and R', represented by polyhydroxyalkyl, alkoxyalkyl and hydroxyalkoxy alkyl, there may be mentioned the groups:
—$CH_2$—$CH_2$—$OCH_3$
—$CH_2$—$CHOH$—$CH_2OH$
—$CH_2$—$CH_2$—$O$—$CH_2$—$CH_2OH$
—$CH_2$—$CH_2$—$CH_2$—$O$—$CH_3$.

The compounds according to the invention which are particularly preferred are those in which X denotes a chlorine atom.

The compounds of formula (I) according to the invention may be prepared in accordance with various preparative processes.

A first process may consist in reacting an aliphatic amine of formula $RNH_2$ with a dihalogenated p-nitroaniline of the formula (II) at a temperature of between 20° and 180° C., optionally in the presence of a solvent such as water, lower alcohols, dioxane, ethylene glycol ethers or diethylene glycol ethers, according to the following reaction scheme:

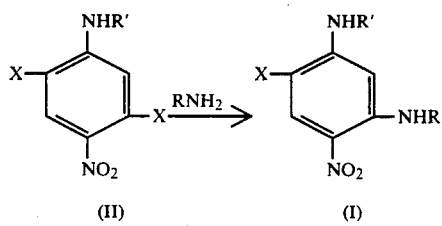

The compounds of formula (II) are obtained using processes which are known per se. The compound (II) may be prepared by starting with the dihalogenated aniline of formula (III), which is converted to a monoarylsulphonamide of formula (IV) by the action of an arylsulphonyl chloride in accordance with the process described in French Pat. No. 1,491,617. The intermediate compound (IV) is nitrated by means of concentrated nitric acid in dilute acetic acid in the presence of sodium nitrite and by heating under reflux to form the compound of formula (V) according to the following reaction scheme:

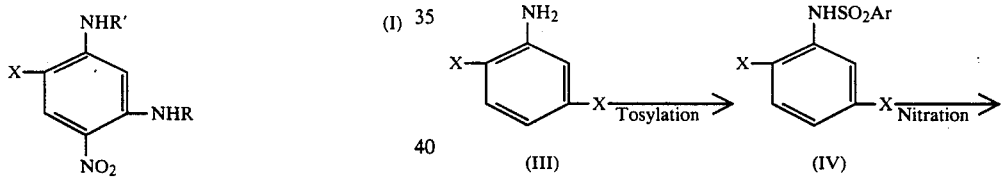

By subjecting the compound of formula (V) to acid hydrolysis as described in French Pat. No. 1,491,617, the compounds of formula (II) is obtained, in which R' denotes H.

By reacting a halide of formula YR', where Y denotes a halogen atom and R' has the meaning indicated for formula (I), with the compound of formula (V) in the presence of potassium carbonate in a solvent such as dimethylformamide, a compound of formula (VI) is obtained and this, by means of acid hydrolysis, leads to the compound of formula (II) in which R' has the meanings referred to above with the exception of H, according to the following reaction scheme:

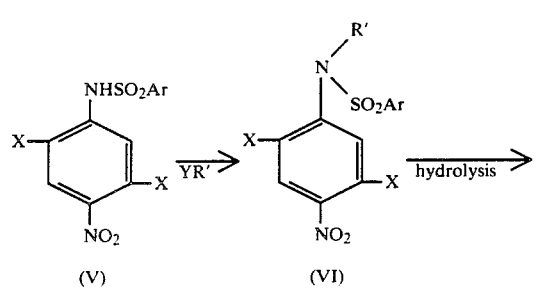

(V) ... (VI) ... hydrolysis →

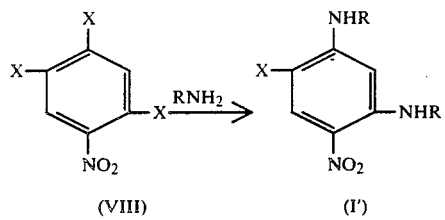

(VIII) (I')

The intermediate compounds corresponding to the formula (II):

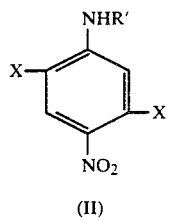

(II)

(II)

in which R' denotes a $C_1-C_6$ alkyl, polyhydroxy $(C_2-C_6)$alkyl, hydroxy$(C_2-C_4)$alkoxy$(C_1-C_4)$alkyl, $(C_1-C_3)$alkoxy$(C_1-C_6)$alkyl radical or an amino$(C_1-C_6)$alkyl radical optionally substituted on the nitrogen atom, and X is a halogen atom, are new and form another subject of the invention.

A second process for the preparation of the compounds according to the invention may consist in reacting an aliphatic amine of formula $R'NH_2$, in which R' has the meaning indicated in formula (I), with a dihalogenated o-nitroaniline of formula (VII) at a temperature of between 20° and 180° C., optionally in the presence of a solvent such as water, the lower alcohols, dioxane, ethylene glycol ethers or diethylene glycol ethers, according to the following reaction scheme:

This also applies to the compounds of formula VII

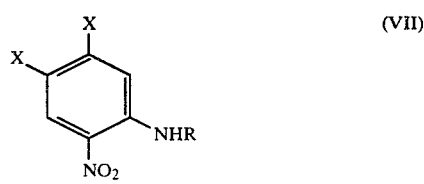

(VII)

in which R denotes a $(C_1-C_3)$alkoxy$(C_1-C_6)$alkyl or hydroxy$(C_2-C_4)$alkoxy$(C_1-C_4)$alkyl radical, and X denotes halogen, which are also new.

The substituent on the nitrogen atom may be a group defined in connection with the compounds of formula I.

The compounds of formula (I) defined above can be used essentially for dyeing keratinic fibres and especially human hair.

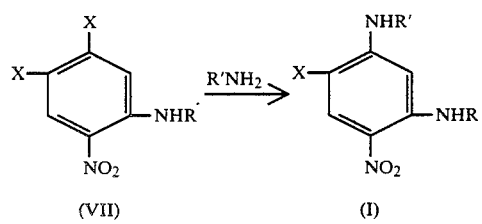

(VII) (I)

The compound (VII) in which R is other than the hydrogen atom, is obtained by the reaction of an amine of formula $RNH_2$, in which R has the meaning indicated in formula (I), with 2,4,5-trihalonitrobenzene.

When R denotes a hydrogen atom, the compound of formula (VII) is obtained by the action of $NH_3$ in the presence of alcohol with the 2,4,5-trihalonitrobenzene, or by any other method described in the literature (Beil. 12 p. 734 and E II 12, p. 399; Beil. 12, p. 741 or E III, p. 1676).

When, in formula (I), R has the same meaning as R', which is other than hydrogen, a third process for the preparation of the compounds according to the invention may consist in reacting the amine $RNH_2$ with the 2,4,5-trihalonitrobenzene, optionally in the presence of a solvent such as those defined above, according to the following reaction scheme:

In this application, these compounds are employed in compositions which are essentially characterized in that they contain, in a cosmetically acceptable solvent medium, at least one compound corresponding to the formula (I) in sufficient proportions for direct dyeing of keratinic fibres or for imparting complementary highlights to the base colour produced by oxidative development of oxidation dyes in the case where they are used in oxidation dyeing compositions.

These compositions contain the compounds according to the invention in proportions of between 0.001 and 5% by weight, and preferably between 0.01 and 3% by weight relative to the total weight of the dye composition.

They may contain anionic, cationic, nonionic or amphoteric surface-active agents or a mixture thereof. These surface-active agents are present in the compositions of the invention in proportions which are preferably between 0.5 and 55% by weight, and especially between 4 and 40% by weight relative to the total weight of the composition.

The cosmetically acceptable medium generally consists of water, but it is also possible to add organic solvents to these compositions to dissolve the compounds which might not be adequately soluble in water. Among these solvents there may be mentioned benzyl and phenylethyl alcohols, lower alkanols such as ethanol and isopropanol, polyols such as glycerol, glycols or glycol ethers such as 2-butoxyethanol, ethylene glycol, ethylene glycol monoethyl ether, propylene glycol, diethylene glycol monoethyl ether and diethylene glycol monomethyl ether, as well as similar products and a mixture thereof. These solvents are preferably present in proportions ranging from 1 to 75% by weight and especially from 5 to 50% by weight relative to the total weight of the composition.

The compositions may be thickened preferably with compounds chosen from sodium alginate, gum arabic, xanthane gum, cellulose derivatives such as methyl cellulose, hydroxyethyl cellulose, hydroxypropyl methyl cellulose, carboxymethyl cellulose and various polymers which function as thickeners, such as more especially acrylic acid derivatives. It is also possible to use inorganic thickening agents such as bentonite. These thickening agents are preferably present in proportions of between 0.1 and 10% by weight, and especially between 0.5 and 3% by weight relative to the total weight of the composition.

The compositions according to the invention may also contain various adjuvants which are usually employed in hair-dyeing compositions, such as penetrating agents, sequestering agents, film-forming agents, buffers and perfumes.

These compositions may be presented in various forms such as a liquid, cream, gel or any other suitable form for performing a hair-dyeing operation. They may also be packaged in aerosol bottles in the presence of a propellent agent.

The pH of these dye compositions may be between 3 and 11.5 and preferably between 5 and 11.5. It is adjusted to the desired value by means of an alkalifying agent such as ammonia, sodium, potassium or ammonium carbonates, sodium or potassium hydroxides, alkanolamines such as mono-, di- or triethanolamine, alkylamines such as ethylamine or triethylamine, or by means of an acidifying agent such as phorphoric, hydrochloric, tartaric, acetic, lactic or citric acids.

When the compositions are intended to be used in a process for direct hair-dyeing, they may contain, in addition to the dyes according to the invention, other direct dyes such as azo dyes such as 4-amino-2'-methyl-4'-N,N-($\beta$-hydroxyethyl)aminophenylazobenzene, or anthraquinone dyes such as, for example, 1,4,5,8-tetraaminoanthraquinone, or nitro dyes from the benzene series which are other than the compounds of formula (I), and especially the following compounds:
2-methyl-6-nitroaniline,
3-nitro-4-aminophenol,
3-nitro-4-N-$\beta$-hydroxyethylaminophenol,
3-nitro-4-amino-6-methylphenol,
3-amino-4-nitrophenol,
2-amino-3-nitrophenol,
3-nitro-6-N-$\beta$-hydroxyethylaminoanisole,
3-N-$\beta$,$\gamma$-dihydroxypropylamino-4-nitroanisole,
(3-N-methylamino-4-nitro)phenoxyethanol,
(3-N-methylamino-4-nitro)phenyl-$\beta$,$\gamma$-dihydroxypropyl ether,
N,N'-($\beta$-hydroxyethyl)nitro-para-phenylenediamine,
3-nitro-4-N'-methylamino-N,N-di-$\beta$-hydroxyethylaniline,
(3-nitro-4-N-$\beta$-hydroxyethylamino)phenoxyethanol, and
(3-nitro-4-N-$\beta$-hydroxyethylamino)phenyl $\beta$,$\gamma$-dihydroxypropyl ether.

The concentrations of these direct dyes other than the dyes of formula (I) may be between 0.001 and 5% by weight relative to the total weight of the composition.

An especially advantageous embodiment consists in the use of the dyes of formula (I) with blue or violet nitrobenzene dyes corresponding to the formula (IX):

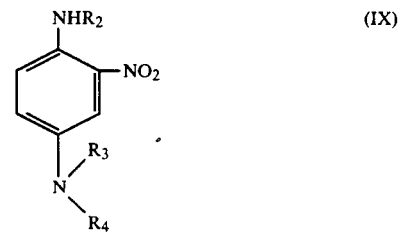

in which $R_2$ denotes a hydrogen atom, a lower alkyl radical preferably containing 1 to 4 carbon atoms, a monohydroxyalkyl radical preferably containing 2 to 4 carbon atoms or a polyhydroxyalkyl radical preferably containing 2 to 4 carbon atoms, or $(C_1-C_4)$alkoxy; and $R_3$ and $R_4$ have individually the same meanings as $R_2$ but may not denote a hydrogen atom.

These dyes may be used in the form of free bases or of salts.

Blue or violet nitrobenzene dyes which are especially advantageous and which may be used with the compounds of formula (I) are chosen from:
(2-N-methylamino-5-N,N-bis-$\beta$-hydroxyethylaminonitrobenzene,
2-N-methylamino-5-(N-methyl-N-$\beta$-hydroxyethyl)aminonitrobenzene,
2-N-$\beta$-hydroxyethylamino-5-N,N-bis-$\beta$-hydroxyethylaminonitrozene,
2-N-$\beta$-hydroxyethylamino-5-(N-methyl-N-$\beta$-hydroxyethyl)aminonitrobenzene,
2-N-$\gamma$-hydroxypropylamino-5-N,N-bis-$\beta$-hydroxyethylaminonitrobenzene,
2-N-methylamino-5-(N-methyl-N-$\beta$,$\gamma$-dihydroxypropyl)aminonitrobenzene
2-amino-5-N,N-bis-$\beta$-hydroxyethylaminonitrobenzene,
4-(N-ethyl-N-$\beta$-hydroxyethyl)amino-1-$\beta$-hydroxyethylamino-2-nitrobenzene,
1-$\beta$,$\gamma$-dihydroxypropylamino-2-nitro-4-(N-methyl-N-$\beta$-hydroxyethyl)aminobenzene, and
1-$\beta$-methoxyethylamino-2-nitro-4-di-$\beta$-hydroxyethylaminobenzene.

These dyes are present in the compositions according to the invention in proportions which are indicated above.

The process for dyeing keratinic fibres, especially human hair, employing these dyes and the compositions indicated above, consists in applying the compositions to the said fibres for an application time of 5 to 40 minutes, in rinsing them, if appropriate washing them, rinsing them again and in drying them.

Another embodiment of the compositions according to the invention is the use in the form of a dyeing hair-setting lotion which imparts a slight colour to hair and improves the retention of the setting all at the same time. In this case it is in the form of an aqueous, alcoholic or aqueous-alcoholic solution containing at least one cosmetic resin, and its application takes place on damp hair, previously washed and rinsed, which may, if appropriate, be wound onto rollers and then dried.

The cosmetic resins used in the setting lotions may be, in particular, polyvinylpyrrolidone, crotonic acid/vinyl acetate, vinylpyrrolidone/vinyl acetate, maleic anhydride/butyl vinyl ether and maleic anhydride/methyl vinyl ether copolymers, as well as any other cationic, anionic, nonionic or amphoteric polymer which is usually employed in a composition of this kind. These cosmetic resins form part of the compositions of the invention in a proportion of 1 to 3% by weight, and preferably from 1 to 2% by weight based on the total weight of the composition.

When the compositions according to the invention form oxidation dyeing compositions, the compounds corresponding to formula (I) are essentially employed with a view to imparting complementary highlights to the final colour.

These compositions then contain precursors of an oxidation dye, in combination with at least one nitro dye of formula (I). They may contain, for example, p-phenylenediamines such as p-phenylenediamine, p-tolylenediamine, 2,6-dimethyl-p-phenylenediamine, 2,6-dimethyl-3-methoxy-p-phenylenediamine, N-$\beta$-methoxyethyl-p-phenylene-diamine, 4-N,N-di-$\beta$-hydroxyethylaminoaniline or 4-(N-ethyl-N-carbamylmethyl-)aminoaniline, and salts thereof.

They may also contain para-aminophenols such as, for example, para-aminophenol, N-methyl-para-aminophenol, 2-chloro-4-aminophenol, 3-chloro-4-aminophenol and their salts.

These compositions may also contain heterocyclic pyridine or morpholine derivatives such as, for example, 2,5-diaminopyridine or 7-aminobenzomorpholine.

As is well known, oxidation dyeing compositions containing the nitro dyes of formula (I) may optionally contain, in combination with the precursors of the para-type oxidation dyes, precursors of ortho-type dyes, as well as couplers which are well known in the state of the art. As couplers, there may be mentioned in particular: meta-diphenols such as resorcinol, 2-methylresorcinol, meta-aminophenols such as meta-aminophenol, 2-methyl-5-aminophenol, 2methyl-5-N-($\beta$-hydroxyethyl)aminophenol, 6-hydroxybenzomorpholine and their salts, meta-phenylenediamines such as (2,4-diamino)phenoxyethanol, 4-N-$\beta$-hydroxyethylamino-2-aminoanisole, 6-aminobenzomorpholine, N-(2-$\beta$-hydroxyethylamino-4-amino)phenoxyethanol, (2,4-diaminophenyl) $\beta,\gamma$-dihydroxypropyl ether and their salts, meta-acylaminophenols, meta-ureidophenols, and meta-carbalkoxyaminophenols, such as 2-methyl-5-acetylaminophenol, 2-methyl-5-ureidophenol or 2-methyl-5-carbethoxyaminophenol.

Lastly, there may be mentioned, as other couplers which can be used: $\alpha$-naphthol, couplers containing an active methylene group such as diketonic compounds and pyrazolones and heterocyclic compounds derived from pyridine, such as, for example 2,4-diaminopyridine, as well as their salts.

In addition, these compositions contain precursors of oxidation dyes, reducing agents such as, more particularly, sodium sulphite, thioglycolic acid, thiolactic acid, sodium bisulphite, ascorbic acid and hydroquinone. These antioxidants are present proportions of between 0.05 and 1.5% by weight relative to the total weight of the composition.

The precursors of oxidation dyes may be used in the compositions of the invention at concentrations of between 0.001 and 5% by weight, and preferably between 0.03 and 2% by weight based on the total weight of the composition. The couplers may be present in proportions of between 0.001 and 5% by weight, and preferably between 0.015 and 2% by weight.

The pH of these compositions is preferably between 7 and 11.5 and is adjusted by means of the alkalifying agents defined above.

The process of dyeing keratinic fibres, especially human hair, employing an oxidation dyeing composition consists in applying to hair the dye composition comprising the dye according to the invention and the dye precursors at the same time and in developing the colour by means of an oxidizing agent present in the dye composition or applied to the hair in a second stage.

The oxidizing agent is preferably chosen from hydrogen peroxide, urea peroxide and persalts, and a 20-volume hydrogen peroxide solution is used in particular.

Once the composition containing the oxidizing agent has been applied to the keratinic fibres, it is left in place for 10 to 50 minutes, and preferably 15 to 30 minutes, whereupon the keratinic fibres are rinsed, are washed with a shampoo if appropriate, are rinsed again and dried.

The compounds of formula (I) may also be applied in multistage processes comprising at least one stage consisting in applying the dye of formula (I) to the fibres under conditions and in proportions which are sufficient to colour them.

The following examples are intended to illustrate the invention without, however, being of a limiting nature.

EXAMPLE OF PREPARATION A

Preparation of the 2,5-dichloro-4-nitroaniline intermediate

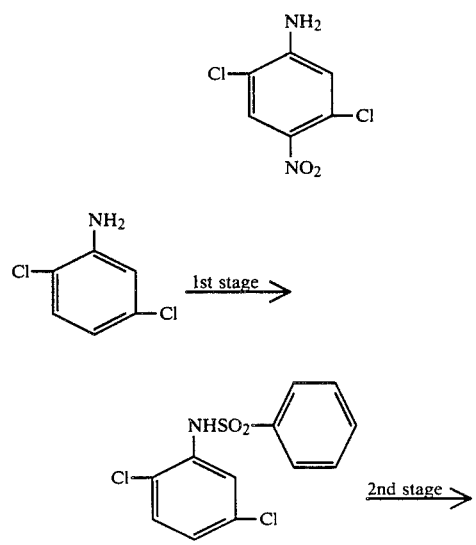

-continued

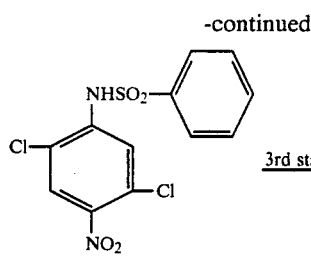

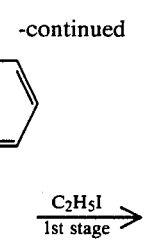

1st stage: Preparation of 2,5-dichloro-N-benzenesulphonylaniline 1 mole (162 g) of 2,5-dichloroaniline is dissolved in 650 ml of pyridine, and 1.1 mole (138 ml) of benzenesulphonyl chloride is added, the temperature being between 35° and 45° C. After 2 hours' heating, the reaction mixture is poured into a mixture of 2 kg of ice in 2 l of water to which 550 ml of concentrated hydrochloric acid have been added. The precipitate obtained in this manner is filtered off and washed with water. An insoluble material is removed by a treatment with normal sodium hydroxide solution. After neutralization with concentrated hydrochloric acid, the expected product precipitates from the filtrate. It melts at 132° C.

2nd stage: Preparation of 2,5-dichloro-4-nitro-N-benzenesulphonylaniline

To 825 ml of acetic acid diluted with an equal volume of water are added: 2.8 g of sodium nitrite, 0.41 mole (125 g) of 2,5-dichloro-N-benzenesulphonylaniline prepared in the previous stage and 2.44 moles (102 ml) of nitric acid (d=1.52). The reaction mixture is heated under reflux for 1 hour. After the reaction mixture has cooled, the expected product is filtered off. It is washed with water and is then recrystallized from acetic acid. It melts at 180° C.

3rd stage: Preparation of 2,5-dichloro-4-nitroaniline 0.44 mole (154 g) of 2,5-dichloro-4-nitrobenzenesulphonylaniline prepared in the previous stage is suspended in 600 ml of concentrated sulphuric acid. After 24 hours' stirring at ambient temperature, the reaction mixture is poured onto 5 kg of ice. The expected product precipitates. After being washed to neutrality and dried, it melts at 156° C.

Analysis of the product obtained gives the following results:

| Analysis | Calculated for $C_6H_4Cl_2N_2O_2$ | Found |
|---|---|---|
| C | 34.78 | 34.62 |
| H | 1.93 | 1.98 |
| N | 13.53 | 13.40 |
| O | 15.46 | 15.66 |
| Cl | 34.30 | 34.24 |

EXAMPLE OF PREPARATION B

Preparation of the 2,5-dichloro-4-nitro-N-ethylaniline intermediate

1st stage: Preparation of 2,5-dichloro-4-nitro-N,N-(ethylbenzenesulphonyl)aniline A mixture consisting of 0.29 mole (107 g) of 2,5-dichloro-4-nitro-N-benzenesulphonylaniline, 0.3 mole (41 g) of potassium carbonate and 0.6 mole (62.4 ml) of ethyl iodide in 600 ml of dimethylformamide is heated for 8 hours at 110° C. The reaction mixture is poured into 2.5 kg of iced water. After filtration and washing, the product obtained is recrystallized from 450 ml of acetic acid. After drying it melts at 125° C.

2nd stage: Preparation of 2,5-dichloro-4-nitro-N-ethylaniline 0.23 ole (84.7 g) of 2,5-dichloro-4-nitro-N,N-(ethylbenzenesulphonyl)aniline prepared in the previous stage is added to 340 ml of concentrated sulphuric acid at 0° C.; the temperature rises to 20° C. After 4 hours' stirring, the reaction mixture is poured into iced water. The expected product precipitates. After being washed to neutrality and dried under vacuum, it is recrystallized from benzene. It melts at 105° C.

Analysis of the product obtained gives the following results:

| Analysis | Calculated for $C_8H_8N_2O_2Cl_2$ | Found |
|---|---|---|
| C | 40.88 | 40.94 |
| H | 3.43 | 3.48 |
| N | 11.92 | 11.90 |
| O | 13.61 | 13.76 |
| Cl | 30.16 | 30.05 |

EXAMPLE OF PREPARATION C

Preparation of
2-chloro-β-(β'-hydroxyethoxy)ethylamino-4-nitro-N-ethylaniline 0.01 mole (2.35 g) of 2,5-dichloro-4-nitro-N-ethylaniline is heated in 10 ml of β-(β'-hydroxyethoxy)ethylamine for 30 minutes on a steam bath.

After cooling, the reaction mixture is diluted with 100 ml of iced water. The expected product precipitates. After being dried, it is recrystallized from ethyl acetate, and a hot filtration enables an insoluble black product to be removed. It melts at 100° C.

Analysis of the product obtained gives the following results:

| Analysis | Calculated for $C_{12}H_{18}N_3O_4Cl$ | Found |
|---|---|---|
| C | 47.45 | 47.24 |
| H | 5.97 | 6.02 |
| N | 13.83 | 13.80 |
| O | 21.07 | 21.21 |
| Cl | 11.67 | 11.91 |

EXAMPLE OF PREPARATION D

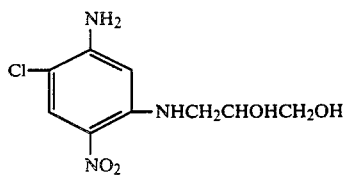

Preparation of
2-chloro-5-N-β,γ-dihydroxypropylamino-4-nitroaniline 0.025 mole (5.14 g) of 2,5-dichloro-4-nitroaniline and 7.5 g of 3-amino-1,2-propanediol are heated to 110° C. in 15 ml of diethylene glycol dimethyl ether to which 5 ml of water have been added.

Heating is continued for 6 hours. After dilution of the reaction mixture with 150 ml of iced water, the expected product precipitates. After filtration and drying, it is recrystallized from a mixture of dioxane and ethanol. It melts at 205° C.

Analysis of the product obtained gives the following results:

| Analysis | Calculated for $C_9H_{12}N_3O_4Cl$ | Found |
|---|---|---|
| C | 41.31 | 41.33 |
| H | 4.62 | 4.68 |
| N | 16.06 | 16.11 |
| O | 24.46 | 24.73 |
| Cl | 13.55 | 13.68 |

EXAMPLE OF PREPARATION E

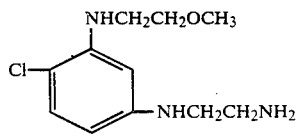

Preparation of
2-chloro-5-β-aminoethylamino-4-nitro-N-β-methoxyethylaniline hydrochloride 1st stage: Preparation of 4,5-dichloro-2-nitro-N-β-aminoethylaniline 0.13 mole (30.6 g) of 1,2,4-trichloro-5-nitrobenzene is added to a solution of 78 g of ethylenediamine in 100 ml of 96° ethanol and 117 ml of water. After 1 h 30 min of heating under reflux, the reaction mixture is cooled. After dilution with iced water, the expected product precipitates. It melts at 84° C.-87° C.

2nd stage: Preparation of 2-chloro-5-β-aminoethylamino-4-nitro-N-β-methoxyethylaniline hydrochloride 0.1 mole (28.6 g) of 4,5-dichloro-2-nitro-N-β-aminoethylaniline prepared in the 1st stage is heated for 4 h 30 min in 60 ml of 2-methoxyethylamine on a steam bath. After cooling and dilution with 200 ml of iced water, the precipitate is recrystallized from isopropanol. After being dissolved in a hot mixture of water and alcohol to which hydrochloric acid has been added, the expected product precipitates as a hydrochloride. It decomposes at 260°-265° C.

Analysis of the product obtained gives the following results:

| Analysis | Calculated for $C_{11}H_{18}N_4O_3Cl_2$ | Found |
|---|---|---|
| C % | 40.63 | 40.66 |
| H % | 5.58 | 5.29 |
| N % | 17.23 | 17.38 |

EXAMPLE OF PREPARATION F

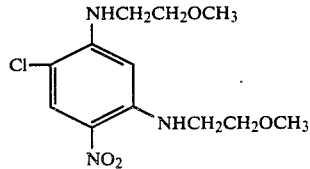

Preparation of
2-chloro-5-β-methoxyethylamino-4-nitro-N-β-methoxyethylaniline 0.9 mole (67.6 g) of 2-methoxyethylamine is heated to reflux in 30 ml of dioxane. 0.15 mole (34 g) of 1,2,4-trichloro-5-nitrobenzene is added portionwise. Heating under reflux is carried out for 4 hours. After cooling, dilution with iced water and neutralization with concentrated hydrochloric acid, the expected product is filtered off. Recrystallized from 96° ethanol, it melts at 106° C.

Analysis of the product obtained gives the following results:

| Analysis | Calculated for $C_{12}H_{18}N_3O_4Cl$ | Found |
|---|---|---|
| C % | 47.45 | 47.66 |
| H % | 5.97 | 6.01 |
| N % | 13.83 | 13.76 |
| O % | 21.07 | 21.23 |
| Cl % | 11.67 | 11.81 |

EXAMPLE OF PREPARATION G

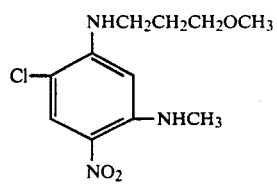

Preparation of 2-chloro-5-methylamino-4-nitro-N-γ-methoxypropylaniline

1st stage: Preparation of 4,5-dichloro-2-nitro-N-methylaniline 0.3 mole (68 g) of 1,2,4-trichloro-5-nitrobenzene is added at room temperature to 200 ml of a 33% strength solution of methylamine in ethanol; the temperature rises to 50° C. The temperature is maintained for 1 hour. After cooling, dilution with 1 liter of iced water and neutralization with concentrated hydrochloric acid, the expected product is filtered off. After purification using refluxing 96° ethanol in order to remove an insoluble material, followed by recrystallization from isopropyl acetate, it melts at 145° C.

Analysis of the product obtained gives the following results:

| Analysis | Calculated for $C_7H_6N_2O_6Cl_2$ | Found |
| --- | --- | --- |
| C % | 38.04 | 38.02 |
| H % | 2.73 | 2.73 |
| N % | 12.67 | 12.79 |
| O % | 14.48 | 14.44 |
| Cl % | 32.08 | 31.97 |

2nd stage: Preparation of 2-chloro-5-methylamino-4-nitro-N-γ-methoxypropylaniline 0.059 mole (13 g) of 4,5-dichloro-2-nitro-N-methylaniline prepared in the previous stage is heated for 4 hours in 40 ml of 3-methoxypropylamine on a steam bath. After dilution with iced water and acidifying with concentrated hydrochloric acid, the expected product is filtered off. Recrystallized from 96° ethanol, it melts at 99° C.

Analysis of the product obtained gives the following results:

| Analysis | Calculated for $C_{11}H_{16}N_3O_3Cl$ | Found |
| --- | --- | --- |
| C % | 48.27 | 48.34 |
| H % | 5.89 | 5.91 |
| N % | 15.35 | 15.38 |
| O % | 17.54 | 17.55 |
| Cl % | 12.95 | 12.90 |

EXAMPLE OF PREPARATION H

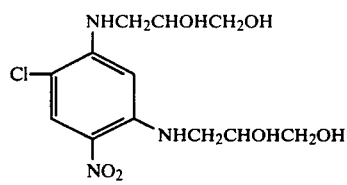

Preparation of 2-chloro-5-β,γ-dihydroxypropylamino-4-nitro-N-β,γ-dihydroxypropylaniline 0.15 mole (34 g) of 1,2,4-trichloro-5-nitrobenzene and 0.9 mole (82 g) of 3-amino-1,2-propanediol are heated to reflux for 5 hours in 30 ml of dioxane.

The reaction mixture is diluted with 1 liter of iced water; after neutralization to pH 7 with concentrated hydrochloric acid, the expected product is isolated from the reaction mixture by column chromatography, a wateralcohol mixture (65% water/35% methanol) being used for elution. After evaporation, a concentrate is obtained and is recrystallized from 95° ethanol. It melts at 129° C.

Analysis of the product obtained gives the following results:

| Analysis | Calculated for $C_{12}H_{18}ClN_3O_6$ | Found |
| --- | --- | --- |
| C % | 42.92 | 42.93 |
| H % | 5.36 | 5.41 |
| N % | 12.52 | 12.59 |
| O % | 28.61 | 28.76 |
| Cl % | 10.58 | 10.37 |

EXAMPLES OF DYE COMPOSITIONS

EXAMPLE 1

The following dye composition is prepared:
2-Chloro-5-N-β,γ-dihydroxypropylamino-4-nitroaniline: 0.05 g
2-Butoxyethanol: 10 g
Cellosize WP 03: 2 g
Cetyldimethylhydroxyethylammonium chloride: 2 g
Triethanolamine as 1% solution in water: 0.5 g
Water q.s.: 100 g
The pH is equal to 7.5.

When applied to bleached hair for 40 minutes at 28° C., this mixture imparts to it a golden yellow shade, after shampooing and rinsing.

EXAMPLE 2

The following dye composition is prepared:
2-Chloro-5-N-β,γ-dihydroxypropylamino-4-nitroaniline: 1.8 g
96° ethanol: 10 g
Alfol C 16/18: 8 g
Lanette E wax: 0.5 g
Cemulsol B: 1 g
Oleoyl diethanolamide: 1.5 g
2-Amino-2-methyl-1-propanol as a 25% solution: 0.3 g
Water q.s.: 100 g
The pH is equal to 10.1.

When applied to bleached hair for 15 minutes at 30° C., this mixture imparts to it a golden yellow shade with beige highlights, after shampooing and rinsing.

EXAMPLE 3

The following dye composition is prepared:
2-Chloro-5-β-(β'-hydroxyethoxy)ethylamino-4-nitro-N-ethylaniline: 0.4 g
2-Butoxyethanol: 20 g
Alfol C 16/18: 8 g
Lanette E wax: 0.5 g
Cemulsol B: 1 g
Oleyl diethanolamide: 1.5 g
2-Amino-2-methyl-1-propanol as 25% solution: 0.3 g
Water q.s.: 100 g
The pH is equal to 10.5.

When applied for 20 minutes at 28° C. to hair 90% of which is naturally grey, this mixture imparts to it a greenish-yellow shade, after shampooing and rinsing.

EXAMPLE 4

The following dye composition is prepared:
2-Chloro-5-β-(β'-hydroxyethoxy)ethylamino-4-nitro-N-ethylaniline: 1 g
96° ethanol: 10 g
Comperlan KD: 2.2 g
Lauric acid: 0.8 g
Ethylene glycol monoethyl ether: 2 g
Monoethanolamine: 1 g
Water q.s.: 100 g
The pH is equal to 8.

When applied to bleached hair for 15 minutes at 30° C., this mixture imparts to it a luminous lemon-yellow shade, after shampooing and rinsing.

EXAMPLE 5

The following dye composition is prepared:
2-Chloro-5-N-β,γ-dihydroxypropylamino-4-nitroaniline: 0.2 g
4-β-Hydroxyethylamino-3-nitrophenol: 0.06 g
4-N,N-bis-β-hydroxyethylamino-2-nitro-N-(β-hydroxyethyl)aniline: 0.15 g
2-Butoxyethanol: 20 g
Cellosize WP 03: 2 g
Ammonium laurylsulphate: 5 g
Ammonia as 4% solution in water: 0.5 g
Water q.s.: 100 g
The pH is equal to 8.3.

When applied to bleached hair for 20 minutes at 28° C., this mixture imparts to it a pink champagne shade, after shampooing and rinsing.

EXAMPLE 6

The following dye composition is prepared:
2-Chloro-5-N-β,γ-dihydroxypropylamino-4-nitroaniline: 0.5 g
4-N,N-bis-β-hydroxyethylamino-2-nitro-N-γ-hydroxypropylaniline: 0.2 g
96° ethanol: 10 g
Lauroylmonoethanolamide: 1.5 g
Lauric acid: 1 g
Cellosize WP 03: 5 g
Monoethanolamine: 2 g
Water q.s.: 2 g
The pH is equal to 9.3.

When applied to dark blonde hair for 30 minutes at 30° C., this mixture imparts to it a light brown shade, after shampooing and rinsing.

EXAMPLE 7

The following dye composition is prepared:
2-Chloro-5-N-β,γ-dihydroxypropylamino-4-nitroaniline: 0.3 g
Para-phenylenediamine: 0.05 g
Para-aminophenol: 0.06 g
Resorcinol: 0.05 g
4-β-Hydroxyethylamino-2-hydroxytoluene: 0.03 g
Alfol C 16/18: 19 g
Eutanol G: 4.5 g
Mergital C.S.: 2.5 g
Ammonium laurylsulphate: 10 g
Cationic polymer containing the following repeat unit:

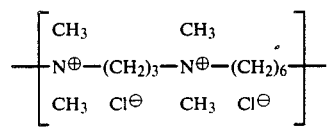

4 g
Benzyl alcohol: 2 g
Ammonia, 22° Bé: 11 ml
Trilon B: 1 g
Sodium bisulphite, 35° Bé: 1.2 g
Water q.s.: 100 g
The pH is 10.1.

100 g of 20-volume hydrogen peroxide are added at the time of use.

When applied for 25 minutes at 30° C. to hair 90% of which is naturally grey, this mixture imparts to it an ash-coloured dark blonde shade, after shampooing and rinsing.

EXAMPLE 8

The following dye composition is prepared:
2-Chloro-5-β-methoxyethylamino-4-nitro-N-β-methoxyethylaniline: 0.47 g
2-Butoxyethanol: 10 g
Cemulsol NP 4: 12 g
Cemulsol NP 9: 15 g
Oleyl alcohol polyglycerolated with 2 moles of glycerol: 1.5 g
Oleyl alcohol polyglycerolated with 4 moles of glycerol: 1.5 g
Triethanolamine q.s. pH=9.1
Water q.s.: 100 g When applied to bleached hair for 20 minutes at 35° C., this mixture imparts to it a pale yellow shade after shampooing and rinsing.

EXAMPLE 9

The following dye mixture is prepared:
2-Chloro-5-β-aminoethylamino-4-nitro-N-β-methoxyethylaniline hydrochloride: 0.066 g
96° ethanol: 11.5 g
20% ammonia: 6.6 g
Cellosize WP 03: 2 g
Ammonium laurylsulphate: 5 g
Water q.s.: 100 g
pH: 10.4.

When applied to permanent-waved hair for 30 minutes at 35° C., this mixture imparts to it a straw-yellow shade after shampooing and rinsing.

EXAMPLE 10

The following dye mixture is prepared:
2-chloro-5-methylamino-4-nitro-N-β-methoxy-
  propylaniline: 0.38 g
96° ethanol: 10 g
Alfol C 16/18: 8 g
Lanette E wax: 0.5 g
Cemulsol B: 1 g
Oleoyldiethanolamide: 1.5 g
Triethanolamine: 0.5 g
Water q.s.: 100 g
pH: 8.

When applied for 30 minutes at 35° C. to hair 90% of which is naturally grey, this mixture imparts to it a pale yellow shade after shampooing and rinsing.

EXAMPLE 11

The following dye mixture is prepared:
2-Chloro-5-β,γ-dihydroxypropylamine-4-nitro-N-β,γ-
  dihydroxypropylaniline: 2.5 g
2-Butoxyethanol: 10 g
20% ammonia: 10 g
Cellosize WP 03: 2 g
Cetyldimethylhydroxyethylammonium chloride: 2 g
Water q.s.: 100 g
pH: 11.1.

When applied for 25 minutes at 30° C. to hair 90% of which is naturally grey, this mixture imparts to it a bright yellow shade, after shampooing and rinsing.

EXAMPLE 12

The following dye mixture is prepared:
2-Chloro-5-β,γ-dihydroxypropylamino-4-nitro-N-β,
  γ-dihydroxypropylaniline: 0.09 g
2-N-β-hydroxyethylamino-5-N,N-bis-β-hydroxye-
  thylaminonitrobenzene: 0.15 g
Tetraaminoanthraquinone: 0.1 g
4-Amino-2'-methyl-4-di-β-hydroxyethylamino-
  phenylazobenzene: 0.05 g
Cellosize WP 03: 2 g
Ammonium laurylsulphate: 5 g
Ethanolamine q.s. pH: 9.7
Water q.s. 100 g When applied for 20 minutes at 35° C. to hair 90% of which is naturally grey, this mixture imparts to it an ash bronze shade to it after shampooing and rinsing.

The trade names used in the examples correspond to the following products:

| | |
|---|---|
| Cellosize WP-03 | hydroxyethyl cellulose sold by the Union Carbide Company |
| Alfol C 16/18 | cetostearyl alcohol sold by the Condea Company |
| Lanette E Wax | sodium cetostearylsulphate sold by the Henkel Company |
| Cemulsol B | ethoxylated castor oil sold by the Rhone-Poulenc Company |
| Comperlan KD | copra fatty acid diethanolamide sold by the Henkel Company |
| Eutanol G | 2-octyldodecanol sold by the Henkel Company |
| Mergital C.S. | cetostearyl alcohol containing 15 moles of E.O., sold by the Henkel Company |
| Trilon B | ethylenediaminetetraacetic acid |
| Cemulsol NP 4 | nonylphenol containing 4 moles of ethylene oxide, sold by the Rhone-Poulenc Company |
| Cemulsol NP 9 | nonylphenol containing 5 moles of ethylene oxide, sold by the Rhone-Poulenc Company. |

We claim:

1. Compound corresponding to the formula:

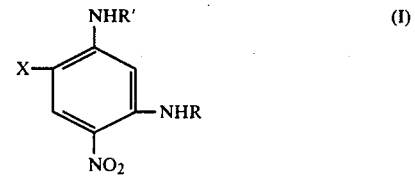

in which x denotes a halogen atom, R and R' denote a hydrogen atom, an alkyl, polyhydroxyalkyl, hydroxyalkoxyalkyl or alkoxyalkyl radical or an aminoalkyl radical optionally substituted on the nitrogen atom provided that at least one of the groups R or R' is a polyhydroxyalkyl, alkoxyalkyl or hydroxyalkoxyalkyl radical.

2. Compound according to claim 1, corresponding to formula (I) in which X denotes chlorine.

3. Compound according to claim 1, wherein R' and/or R denote the group $-CH_2-CHOHCH_2OH$, $-CH_2-CH_2-OCH_2-CH_2-OH$, $-CH_2-CH_2-O-CH_3$ or $-CH_2-CH_2-CH_2-O-CH_3$.

4. Use of the compound as defined in claim 1 for dyeing keratinic fibres and especially human hair.

5. Dye composition for keratinic fibres and especially for human hair containing in a cosmetically acceptable solvent medium, a compound as defined in claim 1, in an amount effective for direct dyeing of the keratinic fibres or for imparting complementary highlights to the base colour in the case of an oxidation dyeing.

6. Composition according to claim 5, wherein the compound of formula (I) is present in proportions of between 0.001 and 5% by weight relative to the total weight of the composition.

7. Composition according to claim 5 containing additionally other direct dyes chosen from azo or anthraquinone dyes, or nitro dyes of the benzene series other than the compounds of formula (I).

8. Composition according to claim 7, wherein the nitro dyes of the benzene series other than the compounds of formula (I) are chosen from the blue or violet nitro dyes corresponding to the formula (IX):

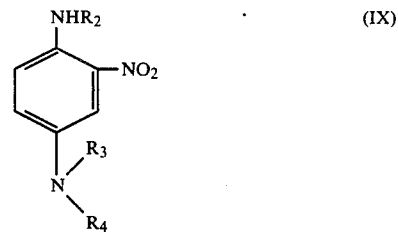

in which $R_2$ denotes a hydrogen atom, an alkyl, hydroxyalkyl, polyhydroxyalkyl or alkoxyalkyl radical, and $R_3$ and $R_4$ have the same meanings as $R_2$ and may not denote hydrogen.

9. Compositions according to claim 5 containing organic solvents chosen from benzyl or phenylethyl alcohols, lower alkanols, polyols, glycols or glycol ethers used by themselves or mixed and present in proportions of between 1 and 75% by weight relative to the total weight of the composition.

10. Composition according to claim 5 containing additionally anionic, cationic, nonionic or amphoteric surface-active agents or a mixture thereof, which are present in proportions of between 0.5 and 55% by weight relative to the total weight of the composition.

11. Composition according to claim 5 containing additionally thickeners present in proportions of between 0.1 and 10% by weight.

12. Composition according to claim 5 under the form of an aqueous, alcoholic or aqueous-alcoholic solution containing at least one cosmetic resin.

13. Dye composition according to claim 5 containing additionally one or more precursors of oxidation dyes.

14. Composition according to claim 13, wherein the precursors of oxidation dyes are p-phenylenediamines, para-aminophenols, heterocyclic pyridine or morpholine derivatives combined or not combined with couplers chosen from meta-diphenols, meta-aminophenols, meta-phenylenediamines, meta-acylaminophenols, meta-ureidophenols, meta-carbalkoxyaminophenols, α-naphthol, diketonic compounds, or pyrazolones and heterocyclic couplers derived from pyridine.

15. Composition according to claim 13 containing also reducing agents which are sodium sulphite, thioglycolic acid, thiolactic acid, sodium bisulphite, ascorbic acid and hydroquinone, which are present in proportions of between 0.05 and 1.5% by weight relative to the total weight of the composition.

16. Composition according to claim 13 wherein the precursors of oxidation dyes are present in proportions of between 0.001 and 5% by weight, the pH of the compositions being between 7 and 11.5.

17. Process for dyeing keratinic fibres, especially human hair, comprising the steps of applying a composition as defined in claim 5 to the said fibres for 5 to 40 minutes, and washing if appropriate, rinsing and drying.

18. Process for dyeing keratinic fibres, and especially human hair, wherein the composition according to claim 13 is applied to the said fibres, in an amount sufficient to develop the colour with the aid of an oxidizing agent present in the dye composition, or applied to the fibres in a second stage.

19. Process for the preparation of the compounds as defined in claim 1, wherein in an aliphatic amine of formula RNH₂ is reacted with a dihalogenated p-nitroaniline corresponding to the formula (II):

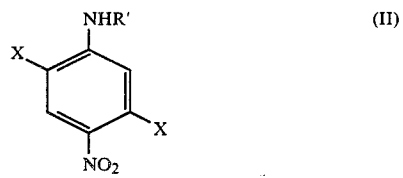

in which R, R' and X have the same meanings as those indicated in any one of claims 1 to 3.

20. Process according to claim 19, wherein the compound of formula (II) is prepared by starting with the dihalogenated aniline converted to a monoarylsulphonamide by reaction with an arylsulphonyl chloride, followed by a nitration using concentrated nitric acid to obtain a compound of formula (V):

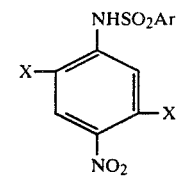

which is then subjected to an acid hydrolysis to produce the compound of formula (II) in which R' denotes H, or that a halide of formula YR' in which Y denotes a halogen atom and R' has the meaning indicated in claim 1 is reacted with the compound of formula (V) in a solvent to produce a compound of formula (VI):

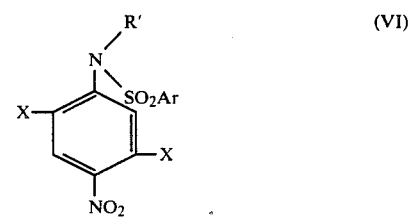

which, by means of acid hydrolysis, produces the compound of formula (II) in which R' denotes an alkyl, polyhydroxyalkyl, alkoxyalkyl or hydroxyalkoxyalkyl radical or an aminoalkyl radical in which the nitrogen atom may be substituted if appropriate.

21. Process for the preparation of the compounds according to claim 1, wherein an aliphatic amine of formula R'NH₂, in which R' has the meaning indicated in claim 1, is reacted with a dihalogenated ortho-nitroaniline of formula (VII):

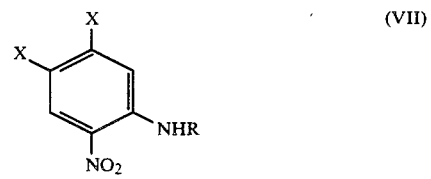

in which R and X have the same meanings as those indicated in any one of claims 1 to 3 at a temperature of between 20° C. and 180° C. in the presence of a solvent.

22. Process for the preparation of a compound defined in claim 1, in which R has the same meaning as R' other than hydrogen, wherein an amine RNH₂ is reacted with a 2,4,5-trihalonitrobenzene in the presence of a solvent if appropriate.

23. Compound corresponding to the formula (II):

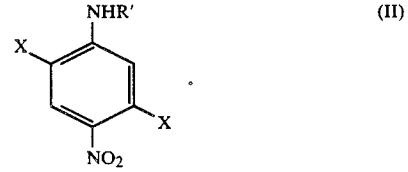

in which X denotes a halogen atom and R' denotes a (C₁-C₆)alkyl, polyhydroxy(C₂-C₆)alkyl, (C₁-C₃)alkoxy(C₁-C₆)alkyl or hydroxy(C₂-C₆)alkoxy(C₁-C₄)alkyl radical or an amino(C₁-C₆)alkyl radical optionally substituted on the nitrogen atom.

24. Compound corresponding to the formula (VII):

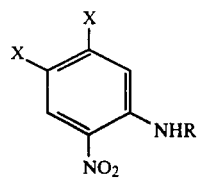
(VII)
in which X denotes halogen and R denotes a $(C_1-C_3)$alkoxy$(C_1-C_6)$alkyl or hydroxy$(C_2-C_4)$alkoxy$(C_1-C_4)$alkyl radical.
* * * * *
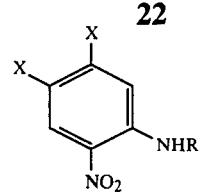
(VII)
in which X denotes halogen and R denotes a $(C_1-C_3)$alkoxy$(C_1-C_6)$alkyl or hydroxy$(C_2-C_4)$alkoxy$(C_1-C_4)$alkyl radical.
* * * * *